United States Patent
De Almeida et al.

(10) Patent No.: US 10,058,565 B2
(45) Date of Patent: Aug. 28, 2018

(54) 2-AMINOETHANOL DIHYDROGEN PHOSPHATE-BASED DIETARY SUPPLEMENT AND SYNTHESIS PROCESS THEREOF

(71) Applicant: ACOLLI S.A., Montevideo (UY)

(72) Inventors: Marcos Vinicius De Almeida, Bauru (BR); Renato Meneguello, Nova Tauá (BR)

( * ) Notice: Subject to any disclaimer, the term of this patent is extended or adjusted under 35 U.S.C. 154(b) by 0 days.

(21) Appl. No.: 15/241,037

(22) Filed: Aug. 18, 2016

(65) Prior Publication Data

US 2017/0296560 A1 Oct. 19, 2017

(30) Foreign Application Priority Data

Apr. 13, 2016 (BR) .......................... 1020160082471

(51) Int. Cl.

| | | |
|---|---|---|
| *A61K 31/661* | (2006.01) | |
| *A61K 31/4172* | (2006.01) | |
| *A61K 31/405* | (2006.01) | |
| *A61K 31/401* | (2006.01) | |
| *A61K 31/355* | (2006.01) | |
| *A23L 33/16* | (2016.01) | |
| *A23L 33/175* | (2016.01) | |
| *A61K 31/07* | (2006.01) | |
| *A23L 33/155* | (2016.01) | |
| *A23L 33/15* | (2016.01) | |
| *A61K 45/06* | (2006.01) | |
| *A61K 31/198* | (2006.01) | |
| *A61K 31/122* | (2006.01) | |

(52) U.S. Cl.
CPC ............ *A61K 31/661* (2013.01); *A23L 33/15* (2016.08); *A23L 33/155* (2016.08); *A23L 33/16* (2016.08); *A23L 33/175* (2016.08); *A61K 31/07* (2013.01); *A61K 31/122* (2013.01); *A61K 31/198* (2013.01); *A61K 31/355* (2013.01); *A61K 31/401* (2013.01); *A61K 31/405* (2013.01); *A61K 31/4172* (2013.01); *A61K 45/06* (2013.01); *A23V 2002/00* (2013.01)

(58) Field of Classification Search
CPC .... A61K 31/661; A61K 31/07; A61K 31/122; A61K 31/198; A61K 31/355; A61K 31/401; A61K 31/405; A61K 31/4172; A61K 45/06; A23L 33/175; A23L 33/16; A23L 33/15; A23L 33/155; A23V 2002/00
USPC .......................................................... 558/1
See application file for complete search history.

(56) References Cited

U.S. PATENT DOCUMENTS

| | | |
|---|---|---|
| 2009/0169675 A1 | 7/2009 | Rowney et al. |
| 2013/0078313 A1 | 3/2013 | Rowney et al. |

FOREIGN PATENT DOCUMENTS

| | | |
|---|---|---|
| CA | 2640796 A1 | 9/2007 |
| EP | 1940518 A1 | 7/2008 |

*Primary Examiner* — Kristin Ann Vajda
(74) *Attorney, Agent, or Firm* — Patent Law Agency, LLC; Peter Ganjian

(57) ABSTRACT

This invention discloses a process for creating an amino acid-based vitamin and mineral dietary supplement and muscle builder having therapeutic activities such as an antioxidant and a metabolic regulator, a regulator of possible cell dysfunctions, an adjuvant of human vitality and well-being and reduction of pain caused by different diseases wherein 2-aminoetanol dihydrogen phosphate is synthesized from phosphorus pentoxide and/or phosphoric acid and/or orthophosphoric acid reacted as monoethanolamine and/or diethanolamine and/or triethanolamine. These are reacted under optimal temperature conditions (−10 to +35° C.) at the specific molar ratios for each reagent used.

2 Claims, No Drawings

2-AMINOETHANOL DIHYDROGEN PHOSPHATE-BASED DIETARY SUPPLEMENT AND SYNTHESIS PROCESS THEREOF

CROSS-REFERENCE TO RELATED APPLICATIONS

This Application is a CONTINUATION application claiming the benefit of priority of the co-pending Federal Republic of Brazil Application No. BR 10 2016 008247 1, filed 13 Apr. 2016, the entire disclosure of which is expressly incorporated by reference in its entirety herein.

TECHNICAL FIELD

The invention relates to a process for creating an amino acid-based vitamin and mineral dietary supplement and muscle builder having therapeutic activities such as an antioxidant and a metabolic regulator, a regulator of possible cell dysfunctions, an adjuvant of human vitality and well-being and reduction of pain caused by different diseases.

BACKGROUND OF THE INVENTION

The massive use of multivitamin dietary supplements described in different ways, in different combinations and concentrations in accordance with the described purpose of each product and manufacturer has been observed in different areas of human activities.

The first dietary supplements were commercialized in 1950. One of the first products was a protein developed and sold by Irvin Johnson in Chicago. Said protein was based on a milk-and-egg protein formulation. Johnson moved to California and changed his name to Rheo Blair. The protein developed by him became popular and a sensation in body-building and movies in the 1960s. Bob Hoffman became Blair's competitor when his company developed a soy-based protein formulation and the "Protein from the Sea" made of seaweed whose best use was as a vomit inducer. As scientific research progressed, the supplement industry burgeoned and, relying on good results obtained from milk and egg proteins, Scott Connelly from Maryland together with a young entrepreneur Bill Phillips from Golden, Colo., developed a protein based supplement that had enough nutrients to replace meals (CA 2640796, EP 1940518, US 200090169675, and US 20130078313).

Multivitamin supplements are vitamin and mineral complexes, essential nutrients that the body is not capable of producing, but which are vital to health and serve as a basis for brain functions, muscle contraction, fluid balance, and energy production. The intended use of said multivitamin supplements is to meet daily nutrient needs of the body to keep the vital functions of the organism in order.

SUMMARY OF THE INVENTION

Due to considerations pertinent to the background art above, it is, therefore, one of the objects of the invention to develop a 2-aminoethanol dihydrogen phosphate-based dietary supplement and a process for synthesis thereof by adding carbonates, sulfates of different minerals, and amino acids of interest.

DETAILED DESCRIPTION OF THE INVENTION

The invention proposed herein is characterized by the description of different steps necessary for implementing the application in question such that it can be fully reproduced by adequate techniques, allowing the full characterization of the functionality of the process claimed herein.

The disclosure is based on different steps described herein that express the best and preferred manner of carrying out the process idealized herein, clarifying the aspects that may be implied in order to clearly determine the scope of protection claimed herein.

Said steps may vary insofar as they do not depart from the spirit and scope of the invention.

Therefore, the products may be created as follows:

In accordance with the present invention, the compound is synthesized from phosphorus pentoxide and/or phosphoric acid and/or orthophosphoric acid reacted as monoethanolamine and/or diethanolamine and/or triethanolamine. These are reacted under optimal temperature conditions (−10 to +35° C.) at the specific molar ratios for each reagent used and described above.

The synthetic pathway described herein uses the reagents disclosed above. In this reaction, they are reacted under constant shaking and an inert argon atmosphere or vacuum or nitrogen or other inert gas bubbled inside the solution with the temperature of its ingredients being between −10° C. and 35° C. and the variable values of phosphorus pentoxide and/or phosphoric acid and/or orthophosphoric acid between 0.001 mol and 20 mol. The values between 0.001 mol and 20 mol are used for the basic reagents (monoethanolamine, diethanolamine, and triethanolamine). After the reaction step, the resulting solution is heated up to the threshold temperature of 230° C. and homogenized with water at the molar ratios between 0.001 mol and 20 mol of water. After homogenization, said solution is crystallized under some organic solvents such as ethanol, methanol, acetone, dimethyl sulfoxide, dimethylformamide, isopropyl alcohol, propyl alcohol, butyl alcohol, among other alcohols such as xylitol, sorbitol, glycerol, and starch at the molar ratios between 0.01 mol and 20 mol of each solvent for each 0.001-25 mol of the homogenized solution. The time needed for crystal formation varies from one hour to six weeks, its final yield increasing over time. After this step, the solution is filtered and dried under dry air at a temperature between 20° C. and 120° C. After this step, the carbonates and sulfates of minerals of interest such as calcium, zinc, magnesium, copper, strontium, boron, molybdenum, iron, chromium, iodine, manganese, and selenium in the proportions that vary from 0.001 to 1,000 mg are added. After this step is finished, the solution is dried again at temperatures between 20° C. and 150° C. After it is completely dried, other vitamin compounds in the following minimum or maximum proportions: B-complex vitamin (0.001 to 5 grams), vitamin A (200 to 50.000 IU), vitamin E (0.01 to 50 mg), and vitamin K2 (0.01 to 40 mg) are added to it for each gram of the obtained compound. Such amino acids of interest as histidine, isoleucina, leucine, lysine, methionine, phenylalanine, threonine, tryptophan, valine, alanine, arginine, aspartic acid, cysteine, glutamic acid, glutamine, ornithine, taurine, proline, serine, and tyrosine in the specific proportions varying from 0.1 mg to 500 mg of each of the compounds specified are also added. Finally, said solution is ground, homogenized, and prepared in different delivery forms for better application in humans.

What is claimed is:

1. A method of making a 2-aminoethanol dihydrogen phosphate-base dietary supplement, comprising reacting 0.001 mol of pyrophosphoric acid with 0.002 mol of basic reagent triethanolamine to form a solution under constant shaking and an inert argon atmosphere with gas bubbled inside the solution at a temperature of −10° C., forming a homogenized solution; crystallizing the homogenized solution under organic solvent acetone at minimum molar ratios varying from 0.01 mol to 20 mol of solvent for each 0.001 mol to 20 mol of homogenized solution; wherein the time needed for crystal formation occurs after six weeks, with the final yield increasing over time, forming a crystallized solution; filtering and drying the crystallized solution under dry air and at a temperature of 20° C.; and adding 0.002 mg of carbonates and sulfates of minerals to the filtered crystallized solution to form aminoethanol dihydrogen phosphate; wherein the carbonates and sulfates of minerals are selected from carbonates and sulfates of calcium, zinc, and magnesium; and drying the aminoethanol dihydrogen phosphate solution at a temperature of 60° C.

2. The method of making a 2-aminoethanol dihydrogen phosphate-based dietary supplement according to claim 1, wherein 0.001 mg of D vitamin compounds are added for each gram of dried aminoethanol dihydrogen phosphate.

* * * * *